US 12,412,764 B2

(12) United States Patent
Matsutori

(10) Patent No.: US 12,412,764 B2
(45) Date of Patent: Sep. 9, 2025

(54) SUBSTRATE-ACCOMMODATING CONTAINER

(71) Applicant: MIRAIAL CO., LTD., Tokyo (JP)

(72) Inventor: Chiaki Matsutori, Tokyo (JP)

(73) Assignee: MIRAIAL CO., LTD., Tokyo (JP)

( * ) Notice: Subject to any disclaimer, the term of this patent is extended or adjusted under 35 U.S.C. 154(b) by 0 days.

(21) Appl. No.: 17/915,904

(22) PCT Filed: Mar. 31, 2020

(86) PCT No.: PCT/JP2020/014929
§ 371 (c)(1),
(2) Date: Sep. 29, 2022

(87) PCT Pub. No.: WO2020/122261
PCT Pub. Date: Jun. 18, 2020

(65) Prior Publication Data
US 2023/0141959 A1 May 11, 2023

(51) Int. Cl.
*H01L 21/673* (2006.01)
(52) U.S. Cl.
CPC .. *H01L 21/67376* (2013.01); *H01L 21/67366* (2013.01); *H01L 21/67373* (2013.01)
(58) Field of Classification Search
CPC ......... H01L 21/67366; H01L 21/67376; H01L 21/67379; H01L 21/67373
USPC ........................................ 206/710–712, 832
See application file for complete search history.

(56) References Cited

U.S. PATENT DOCUMENTS

| 6,216,874 | B1 * | 4/2001 | Bores | H01L 21/67379 211/41.18 |
| 6,382,419 | B1 * | 5/2002 | Fujimori | H01L 21/67369 211/41.18 |
| 6,851,170 | B2 * | 2/2005 | Lappen | H01L 21/68 29/466 |
| 7,703,609 | B2 * | 4/2010 | Nakatogawa | H01L 21/67379 206/711 |
| 11,227,781 | B2 * | 1/2022 | Ogawa | H01L 21/67386 |
| 2003/0029765 | A1 * | 2/2003 | Bhatt | B29C 45/14311 211/41.18 |

(Continued)

FOREIGN PATENT DOCUMENTS

JP 2004214269 A 7/2004
JP 2007088064 A 4/2007
(Continued)

*Primary Examiner* — Chun Hoi Cheung
(74) *Attorney, Agent, or Firm* — Muncy, Geissler, Olds & Lowe, P.C.

(57) ABSTRACT

The container main body includes a tubular wall portion having an opening circumferential portion provided at one end portion and the other end portion being closed, the opening circumferential portion having a container main body opening portion formed therein. The substrate storing space can store a substrate and communicates with the container main body opening portion. A central fixed member is provided to the wall portion of the container main body so as to be removably attached to the wall portion of the container main body. The central fixed member is configured to be locked and fixed to an alignment portion provided at a load port for conveying the substrate stored in the substrate storing space to a processing apparatus.

6 Claims, 7 Drawing Sheets

(56) References Cited

U.S. PATENT DOCUMENTS

| | | | |
|---|---|---|---|
| 2004/0124118 A1 | 7/2004 | Matsutori et al. | |
| 2006/0207916 A1* | 9/2006 | Mimura | G03F 1/66 |
| | | | 206/454 |
| 2008/0041761 A1* | 2/2008 | Nakatogawa | H01L 21/67379 |
| | | | 206/711 |
| 2012/0325707 A1* | 12/2012 | Ogawa | H01L 21/67379 |
| | | | 206/454 |
| 2016/0126122 A1* | 5/2016 | Kanamori | H01L 21/67383 |
| | | | 206/723 |
| 2016/0204011 A1* | 7/2016 | Shigeta | H01L 21/67386 |
| | | | 206/710 |
| 2020/0043755 A1 | 2/2020 | Kai | |
| 2020/0279761 A1* | 9/2020 | Ogawa | H01L 21/67379 |
| 2020/0373180 A1* | 11/2020 | Toda | H01L 21/6734 |
| 2023/0260813 A1* | 8/2023 | Matsutori | H01L 21/67379 |
| | | | 206/710 |

FOREIGN PATENT DOCUMENTS

| | | |
|---|---|---|
| JP | 2008010574 A | 1/2008 |
| JP | 2017092172 A | 5/2017 |
| TW | 201834119 A | 9/2018 |
| WO | WO2007/034654 A1 | 3/2007 |
| WO | WO2014/196011 A1 | 12/2014 |
| WO | WO2019/031142 A1 | 2/2019 |

* cited by examiner

SUBSTRATE-ACCOMMODATING CONTAINER

TECHNICAL FIELD

The present invention relates to a substrate storing container for use in storing, keeping, conveying, transporting, and the like substrates composed of semiconductor wafers or the like.

BACKGROUND ART

As a substrate storing container for storing and conveying substrates composed of semiconductor wafers, one has been known conventionally that includes a container main body and a lid body (see Patent Documents 1 and 2).

The container main body includes a tubular wall portion in which a container main body opening portion is formed at one end portion, and in which the other end portion is closed. A substrate storing space is formed in the container main body. The substrate storing space is formed by being surrounded by the wall portion and can store a plurality of substrates. The lid body can be removably attached to the container main body opening portion and can close the container main body opening portion.

A front retainer is provided at a portion of the lid body that faces a substrate storing space when the container main body opening portion is closed. When the container main body opening portion is closed by the lid body, the front retainer can support edge portions of the plurality of substrates. A back side substrate support portion is provided at the wall portion so as to form a pair with the front retainer. The back side substrate support portion can support edge portions of the plurality of substrates. When the container main body opening portion is closed by the lid body, the back side substrate support portion supports the plurality of substrates in cooperation with the front retainer, thereby retaining the plurality of substrates in a state in which the adjacent substrates are arranged in parallel to be spaced apart by a predetermined interval.

The wall portion of the container main body includes a back wall, an upper wall, a lower wall, and a pair of side walls, and the container main body opening portion is formed by one end portion of the upper wall, one end portion of the lower wall, and one end portions of the side walls. The bottom portion of the container main body of the substrate storing container including the lower wall has abutting portions with which kinematic pins of a load port or the like for conveying the substrates stored in the substrate storing space to the processing apparatus abut. Further, the bottom portion has a central locked portion that is locked and fixed to a central container locking portion of a load port or the like. The central locked portion is positioned substantially equidistant from each of the abutting portions. The central locked portion is fixed to the central container locking portion of the load port or the like, so that the container main body is fixed to the load port or the like in a state of being supported by the kinematic pins of the load port or the like.

Patent Document 1: PCT International Publication No. WO2007-034654

Patent Document 2: Japanese Unexamined Patent Application, Publication No. 2007-088064

DISCLOSURE OF THE INVENTION

Problems to be Solved by the Invention

As described above, the central locked portion is locked to the central container locking portion of the load port or the like, so that the container main body is positioned and fixed to the load port or the like. Therefore, the central locked portion plays an important role in determining the center when the substrates are automatically transferred. Therefore, accuracy of the central locked portion needs to be improved, and the container needs to be fixed during operation of the load port. To fix the container, the container needs to be held to the lower face (reference face side) due to the structure of the central locked portion. The central locked portion has a hole shape and has a predetermined height in a Z direction (vertical direction).

Therefore, when the container main body and the central locked portion are integrally molded, the central locked portion becomes an undercut at the time of releasing the injection mold. Therefore, a complicated structure called a slide structure is required for the mold. As a result, since the operation of the mold becomes complicated, the operation speed needs to be reduced to prevent breakage of the mold. Thus, the molding cycle becomes long, resulting in lower production efficiency. Further, since the structure of the mold becomes complicated, it becomes difficult to form a cooling circuit for the mold for circulating cooling water in the mold to absorb the heat of the molten resin as an optimal circuit at an optimal position, and thus the cooling time is extended.

It is an object of the present invention to provide a substrate storing container that facilitates the formation of a cooling circuit for a mold for circulating cooling water in the mold as an optimal circuit at an optimal position by avoiding a complicated structure of the mold.

Means for Solving the Problems

The present invention relates to a substrate storing container. The substrate storing container includes a container main body, a lid body, and a sealing member. The container main body includes a tubular wall portion having an opening circumferential portion provided at one end portion and the other end portion being closed, the opening circumferential portion having a container main body opening portion formed therein, and a substrate storing space formed by an inner face of the wall portion. The substrate storing space can store a substrate and communicates with the container main body opening portion. The lid body can be removably attached to the opening circumferential portion and can close the container main body opening portion by being in a positional relationship in which the lid body is surrounded by the opening circumferential portion. The sealing member is attached to the lid body and can abut with the lid body and the opening circumferential portion. The sealing member is configured to close the container main body opening portion in cooperation with the lid body by being interposed between the opening circumferential portion and the lid body so as to tightly abut with the opening circumferential portion and the lid body. A central fixed member is provided to the wall portion of the container main body so as to be removably attached to the wall portion of the container main body. The central fixed member is configured to be locked and fixed to an alignment portion provided at a load port for conveying the substrate stored in the substrate storing space to a processing apparatus.

The central fixed member is preferably fixed to the wall portion of the container main body by a fitting structure.

The central fixed member preferably includes a member front portion having an oval shape constituting a portion of the central fixed member on one end portion side of the container main body, and a member rear portion having a rectangular shape constituting a portion of the central fixed member on the other end portion side of the container main body.

The member front portion is preferably engaged with and fixed to the container main body at one position, the member rear portion is preferably engaged with and fixed to the container main body at two positions, and the central fixed member is preferably fitted into the wall portion of the container main body.

The central fixed member is preferably made of a polycarbonate resin. The central fixed member may be made of a cycloolefin polymer resin.

Effects of the Invention

According to the present invention, it is possible to provide a substrate storing container that facilitates the formation of a cooling circuit for a mold for circulating cooling water in the mold as an optimal circuit at an optimal position by avoiding a complicated structure of the mold.

PREFERRED MODE FOR CARRYING OUT THE INVENTION

Figure 1:
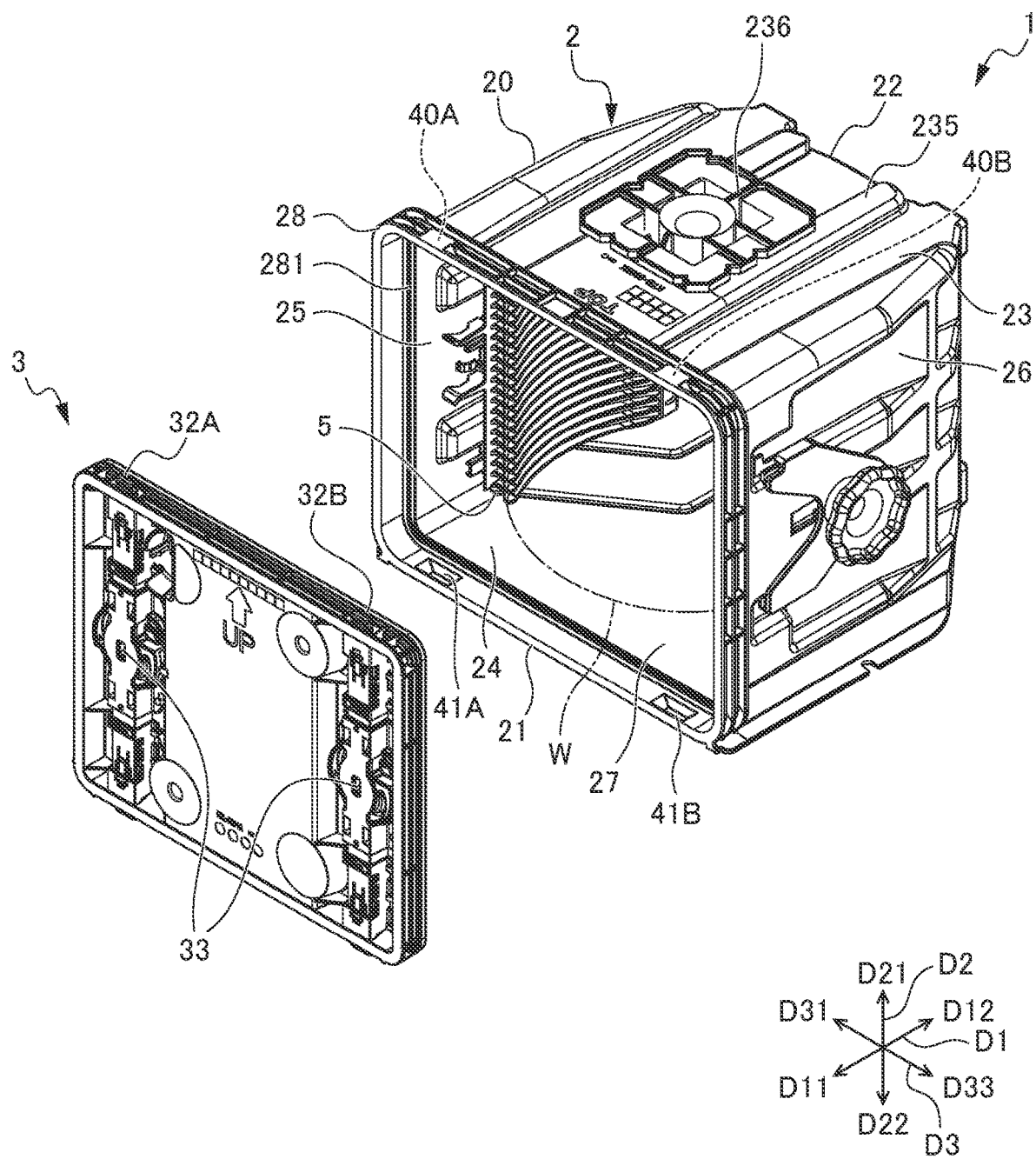
FIG. 1 is an exploded perspective view showing a substrate storing container 1 according to an embodiment of the present invention.
Figure 2A:
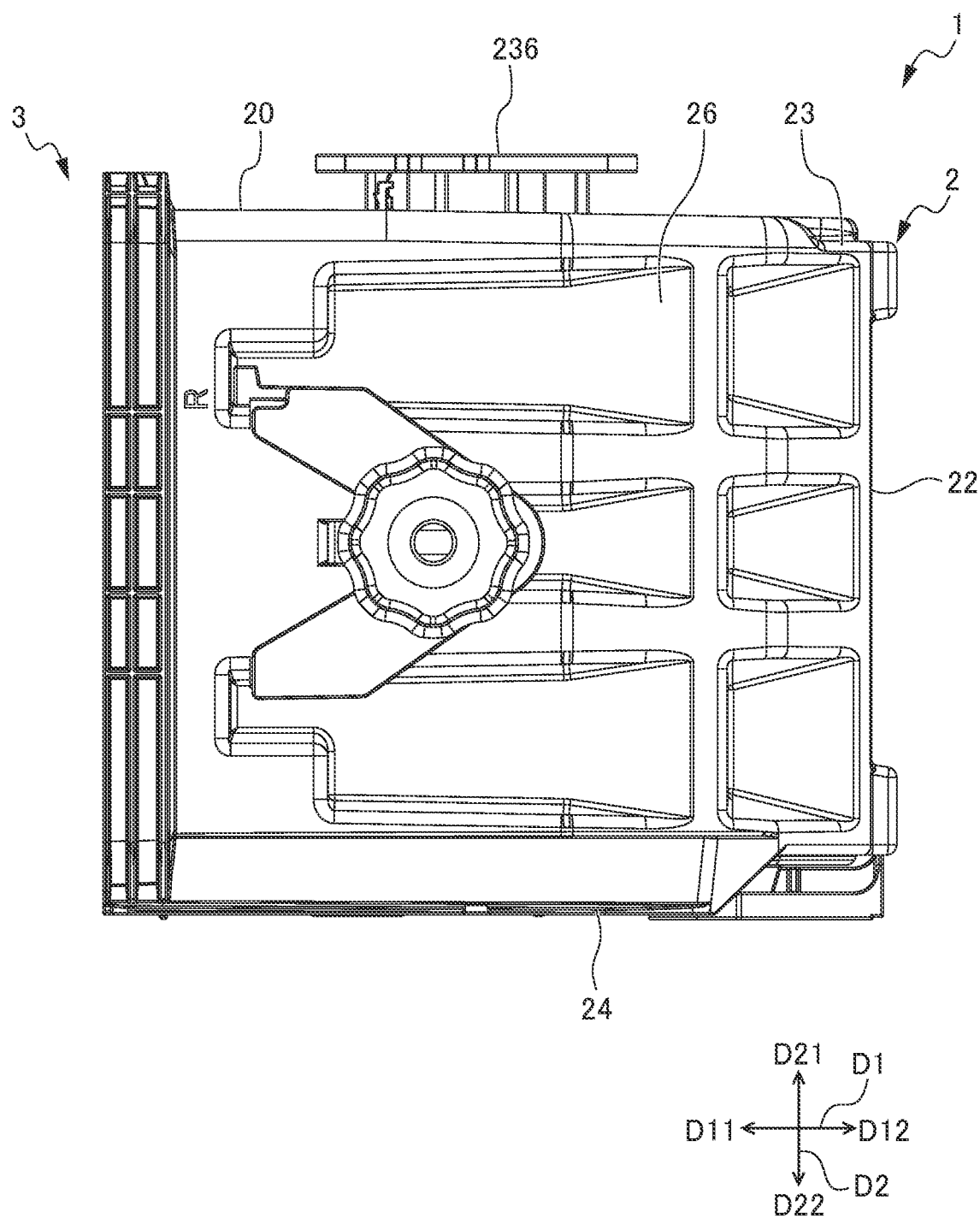
FIG. 2A is a right side view showing the substrate storing container 1 according to the embodiment of the present invention.
Figure 2B:
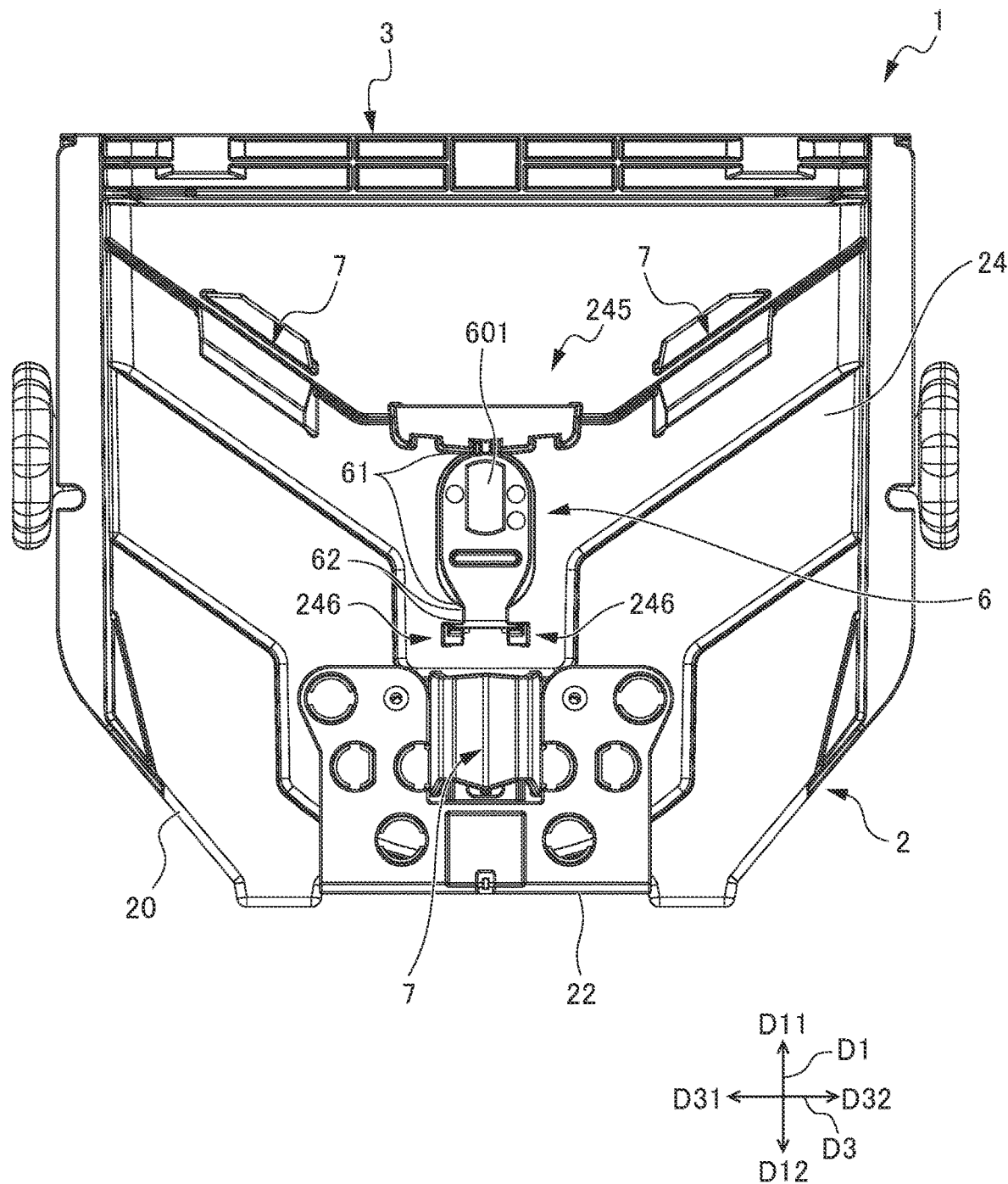
FIG. 2B is a bottom view showing the substrate storing container 1 according to the embodiment of the present invention.
Figure 3:
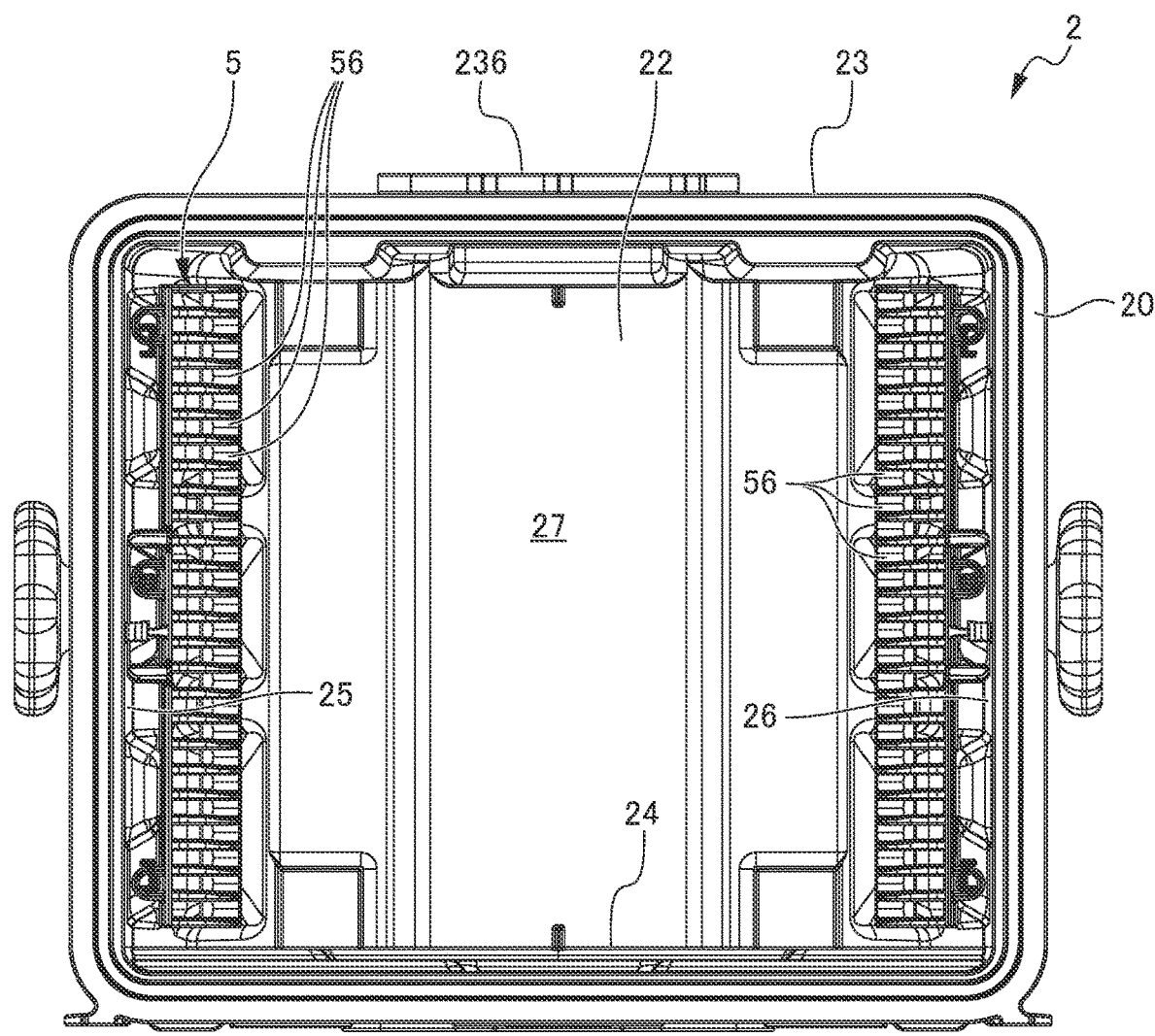
FIG. 3 is an elevation view showing a container main body 2 of the substrate storing container 1 according to the embodiment of the present invention.
Figure 3:
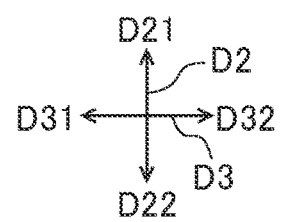

Hereinafter, a substrate storing container 1 according to an embodiment will be described with reference to the drawings. FIG. 1 is an exploded perspective view showing a state in which a substrate W is stored in the substrate storing container 1. FIG. 2A is a right side view showing the substrate storing container 1. FIG. 2B is a bottom view showing the substrate storing container 1. FIG. 3 is an elevation view showing the container main body 2 of the substrate storing container 1.

Herein, for the purpose of illustration, the direction from a container main body 2 to a lid body 3 (described later) (direction from the upper right to the lower left in FIG. 1) is defined as a forward direction D11 and the direction opposite to the direction D11 is defined as a backward direction D12. These directions are collectively defined as a forward/backward direction D1. In addition, the direction from a lower wall 24 to an upper wall 23 (described later) (upper direction in FIG. 1) is defined as an upper direction D21 and the direction opposite to the direction D21 is defined as a lower direction D22. These directions are defined as an upper/lower direction D2. Moreover, the direction from a second side wall 26 to a first side wall 25 (described later) (direction from the lower right to the upper left in FIG. 1) is defined as a left direction D31 and the direction opposite to the direction D31 is defined as a right direction D32. These directions are defined as a left/right direction D3. The drawings show arrows indicating these directions.

The substrate W (see FIG. 1) stored in the substrate storing container 1 is a disk-like silicon wafer, glass wafer, sapphire wafer, or the like, and is a thin member used for industrial use. The substrate W in the present embodiment is a silicon wafer having a diameter of 300 mm.

As shown in FIG. 1, the substrate storing container 1 is used for storing the substrate W composed of a silicon wafer as described above and conveying it in a process in a factory as an in-process container or transporting the substrate by transport means such as land transport means, air transport means, or sea transport means as a shipping container. The substrate storing container 1 includes a container main body 2 and a lid body 3. The container main body 2 includes a substrate support plate-like portion 5 and a back side substrate support portion 56 (see FIG. 3, etc.). The lid body 3 includes a front retainer (not shown).

The container main body 2 includes a tubular wall portion 20 with a container main body opening portion 21 formed at one end portion and the other end portion closed. A substrate storing space 27 is formed in the container main body 2. The substrate storing space 27 is surrounded by the wall portion 20. The substrate support plate-like portion 5 is disposed at a portion of the wall portion 20 that forms the substrate storing space 27. As shown in FIG. 1, a plurality of substrates W can be stored in the substrate storing space 27.

The substrate support plate-like portion 5 is provided at the wall portion 20 so as to form a pair in the substrate storing space 27. When the container main body opening portion 21 is not closed by the lid body 3, the substrate support plate-like portion 5 can support edge portions of the plurality of substrates W by abutting with the edge portions of the plurality of substrates W in a state in which the adjacent substrates W are arranged in parallel to be spaced apart by a predetermined interval. A back side substrate support portion 56 (see FIG. 3, etc.) is provided at the back side of the substrate support plate-like portion 5.

The back side substrate support portion 56 is provided at the wall portion 20 so as to form a pair with the front retainer (not shown) described later in the substrate storing space 27. When the container main body opening portion 21 is closed by the lid body 3, the back side substrate support portion 56 can support the rear edge portions of the plurality of substrates W by abutting with the edge portions of the plurality of substrates W.

The lid body 3 can be removably attached to an opening circumferential portion 28 (see FIG. 1, etc.) forming the container main body opening portion 21 and can close the container main body opening portion 21. The front retainer (not shown) is provided at a portion of the lid body 3 that faces the substrate storing space 27 when the container main body opening portion 21 is closed by the lid body 3. The front retainer (not shown) is provided so as to form a pair with the back side substrate support portion 56 in the substrate storing space 27.

When the container main body opening portion 21 is closed by the lid body 3, the front retainer (not shown) can support the front edge portions of the plurality of substrates W by abutting with the edge portions of the plurality of substrates W. When the container main body opening portion 21 is closed by the lid body 3, the front retainer (not shown) supports the plurality of substrates W in cooperation with the back side substrate support portion 56, thereby retaining the plurality of substrates W in a state in which the adjacent substrates W are arranged in parallel to be spaced apart by a predetermined interval.

The substrate storing container 1 is made of a resin such as a plastic material or the like. If not specifically described, examples of the resin include thermoplastic resins such as polycarbonate, cycloolefin polymer, polyetherimide, polyetherketone, polybutyl terephthalate, polyetheretherketone, and liquid crystal polymer, and alloys thereof. In the case of imparting conductivity to these resins which are molding materials, conductive materials such as carbon fibers, carbon powder, carbon nanotubes, and conductive polymers are selectively added. It is also possible to add glass fibers, carbon fibers, or the like to increase the rigidity.

Figure 4:
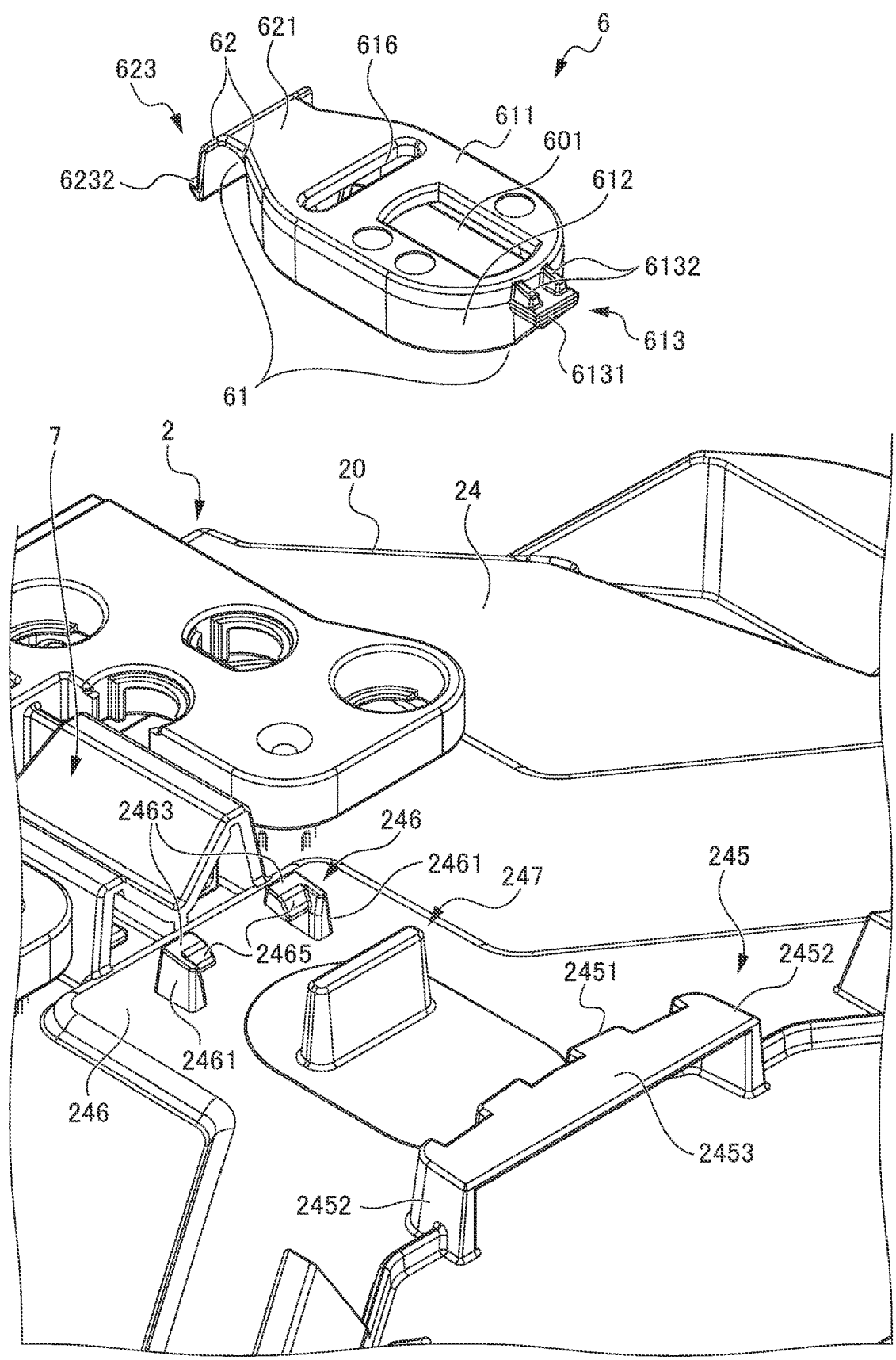
FIG. 4 is an exploded perspective view showing the front portion of a central fixed member 6 provided to the container main body 2 of the substrate storing container 1 according to the embodiment of the present invention.
Figure 5:
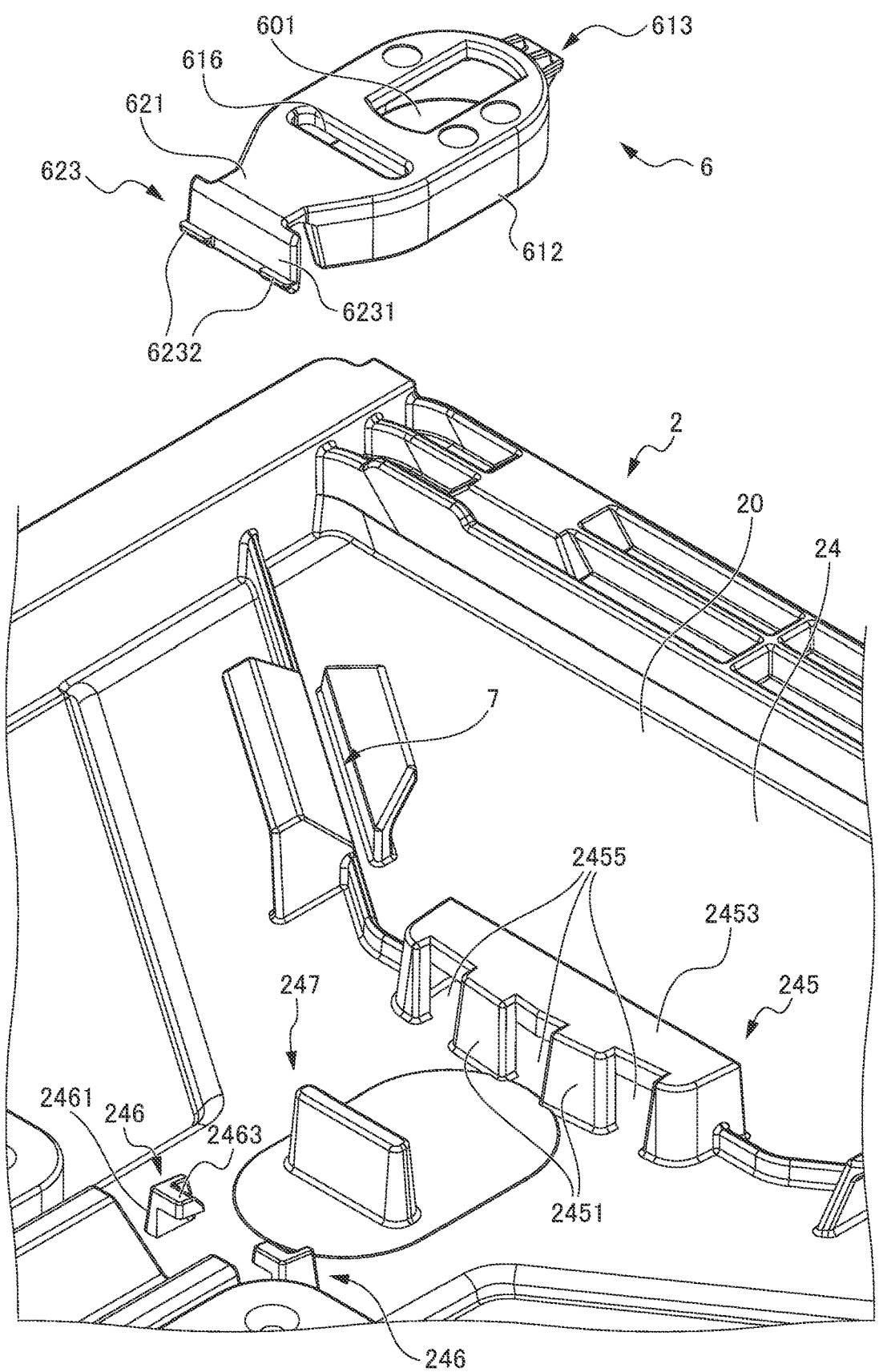
FIG. 5 is an exploded perspective view showing the rear portion of the central fixed member 6 provided to the container main body 2 of the substrate storing container 1 according to the embodiment of the present invention.
Figure 6A:
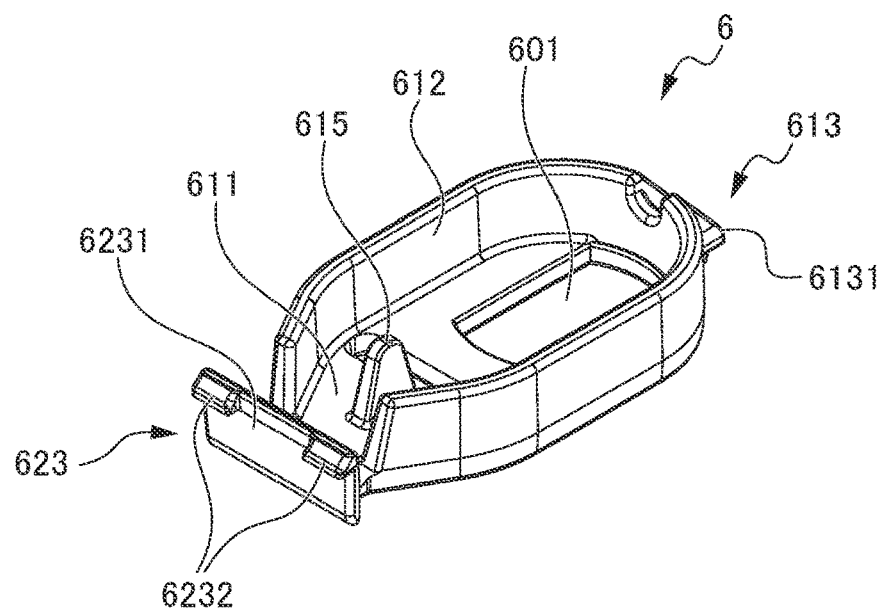
FIG. 6A is a perspective view showing the rear portion of the central fixed member 6 provided to the container main body 2 of the substrate storing container 1 according to the embodiment of the present invention.
Figure 6B:
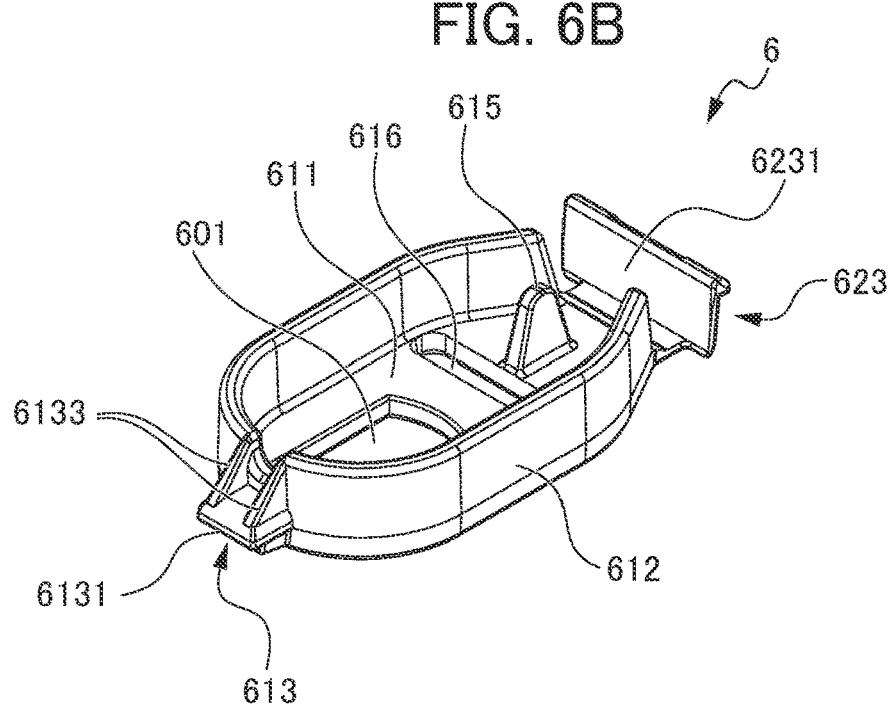
FIG. 6B is a perspective view showing the front portion of the central fixed member 6 provided to the container main body 2 of the substrate storing container 1 according to the embodiment of the present invention.

Each portion is described in detail in the following. FIG. 4 is an exploded perspective view showing the front portion of a central fixed member 6 provided to the container main body 2 of the substrate storing container 1. FIG. 5 is an exploded perspective view showing the rear portion of the central fixed member 6 provided to the container main body 2 of the substrate storing container 1. FIG. 6A is a perspective view showing the rear portion of the central fixed member 6 provided to the container main body 2 of the substrate storing container 1. FIG. 6B is a perspective view showing the front portion of the central fixed member 6 provided to the container main body 2 of the substrate storing container 1.

As shown in FIG. 1, etc., the wall portion 20 of the container main body 2 includes a back wall 22, an upper wall 23, a lower wall 24, a first side wall 25, and a second side wall 26. The back wall 22, the upper wall 23, the lower wall 24, the first side wall 25, and the second side wall 26 are made of the above-described material and are integrally molded.

The first side wall 25 faces the second side wall 26, and the upper wall 23 faces the lower wall 24. The rear edge of the upper wall 23, the rear edge of the lower wall 24, the rear edge of the first side wall 25, and the rear edge of the second side wall 26 are all connected to the back wall 22. The front edge of the upper wall 23, the front edge of the lower wall 24, the front edge of the first side wall 25, and the front edge of the second side wall 26 have a positional relationship opposite the back wall 22, and constitute the opening circumferential portion 28 that forms the container main body opening portion 21 in a substantially rectangular shape.

The opening circumferential portion 28 is provided at one end portion of the container main body 2, and the back wall 22 is located at the other end portion of the container main body 2. The profile of the container main body 2 formed by the outer faces of the wall portion 20 is a box shape. The inner faces of the wall portion 20, i.e., the inner face of the back wall 22, the inner face of the upper wall 23, the inner face of the lower wall 24, the inner face of the first side wall 25, and the inner face of the second side wall 26, form the substrate storing space 27, which is surrounded thereby. The container main body opening portion 21 formed by the opening circumferential portion 28 is in communication with the substrate storing space 27 surrounded by the wall portion 20 and formed inside the container main body 2. The substrate storing space 27 can store a maximum of 25 substrates W.

As shown in FIG. 1, latch engagement concave portions 40A, 40B, 41A, and 41B, which are concave outwardly from the substrate storing space 27, are formed at portions of the upper wall 23 and the lower wall 24 that are proximal to the opening circumferential portion 28. A total of four latch engagement concave portions 40A, 40B, 41A, and 41B are respectively formed near both right and left end portions of the upper wall 23 and the lower wall 24.

As shown in FIG. 1, a rib 235 is provided so as to be integrally formed with the upper wall 23 at the outer face of the upper wall 23. The rib 235 increases the rigidity of the container main body 2.

A top flange 236 is fixed to the central portion of the upper wall 23. The top flange 236 is a member corresponding to a portion of the substrate storing container 1 from which it is hung to be suspended when suspending the substrate storing container 1 by an automated material handling system (AMHS), a person guided vehicle (PGV), etc.

At the central position of the lower wall 24, there are provided the central fixed member 6 having a central through hole 601 formed therein, a front side fixing portion 245 for fixing the central fixed member 6, a rear side fixing portion 246, and a detection central convex portion 247 provided at a position between the front side fixing portion 245 and the rear side fixing portion 246.

The front side fixing portion 245 is provided at a position advanced from the central position of the lower wall 24 in the forward direction D11 by approximately one third of the length between the central position of the lower wall 24 and the front edge of the lower wall 24. The front side fixing portion 245 includes a rear wall 2451 extending in substantially the left/right direction D3 and projecting in the lower direction D22, side walls 2452 extending in the forward direction from both left and right end portions of the rear wall 2451 and projecting in the lower direction D22, and a lower wall 2453 integrally formed with the lower edge of the rear wall 2451 and the lower edges of the side walls 2452 to be integrally connected. The front edges of the side walls 2452 and the front edge of the lower wall 2453 constitute an opening portion that opens toward the forward direction 11. Through holes 2455 passing through in the forward/backward direction D1 are formed at the central portion of the rear wall 2451 and both left and right sides thereof. A front portion engaged portion 613 (described later) is fitted into the central through hole 2455, whereby the front portion engaged portion 613 is engaged with and fixed to the front side fixing portion 245 at this one position.

The rear side fixing portion 246 is provided at a position advanced from the central position of the lower wall 24 in the backward direction D12 by approximately one third of the length between the central position of the lower wall 24 and the rear edge of the lower wall 24. The rear side fixing portion 246 includes a pair of side walls 2461 extending in substantially the forward/backward direction D1 and projecting in the lower direction D22, and lower walls 2463 respectively extending from the rear portions of the pair of side walls 2461 so as to approach each other and be integrally formed with the side walls 2461 to be integrally connected. The front end portion of the lower wall 2463 has an inclined face 2465 that rises in the upper direction D21 toward the forward direction D11. At the lower side of the pair of lower walls 2463, locked plate portions 6232 of a rear portion engaged portion 623 (described later) are respectively disposed, whereby the rear portion engaged portion 623 is engaged with and fixed to the rear fixing portion 246 at two positions, i.e., at both end portions of the rear portion engaged portion 623 in the left/right direction D3. The detection central convex portion 247 is constituted by rectangular wall portions extending in the left/right direction D3 and projecting in the lower direction D22.

The central fixed member 6 is locked and fixed to a boss constituting a container fixing portion provided at a load port (not shown) for conveying the substrates W stored in the substrate storing space 27 to a processing apparatus. The central fixed member 6 is composed of a component independent of the lower wall 24, and is fixed to the lower wall 24 constituting the wall portion 20 of the container main body 2 by a fitting structure.

The central fixed member 6 is made of a resin such as a polycarbonate resin, a cycloolefin polymer resin, a polybutylene terephthalate resin, a polyacetal resin, or a polyetheretherketone resin. In the present embodiment, a polycarbonate resin or a cycloolefin polymer resin is used.

As shown in FIGS. 6A, 6B, etc., the central fixed member 6 includes a member front portion 61 and a member rear portion 62. The member front portion 61 has an oval shape in bottom view, the member rear portion 62 has a rectangular shape in bottom view, and the member front portion 61 and the member rear portion 62 are integrally formed and integrally connected.

A front portion peripheral wall portion 612 projecting in the upper direction D21 is integrally formed with and integrally connected to a front portion bottom portion 611, around the member front portion 61. The front portion peripheral wall portion 612 is provided over the entire peripheral edge portion excluding the rear portion of the member front portion 61. A central through hole 601 composed of a substantially rectangular through hole elongated in the forward/backward direction in plan view is formed at a position adjacent to the forward part of the front portion peripheral wall portion 612. The boss constituting the container fixing portion of the load port (not shown) is inserted into the central through hole 601, the central fixed member 6 is locked to the boss, and the container main body 2 is held and fixed to the reference surface side of the load port.

At the front edge of the front portion peripheral wall portion 612, a front portion engaged portion 613 projecting in the forward direction is integrally formed with and integrally connected to the front portion peripheral wall portion 612. The front portion engaged portion 613 includes a plate-like base portion 6131 that is parallel to the forward/backward direction D1 and the left-right direction D3 and projects from the front edge of the front portion peripheral wall portion 612 in the forward direction D11, a pair of upper ribs 6132 that are integrally formed with the front edge of the front portion peripheral wall portion 612 and the upper face of the base portion 6131 and extend in the forward direction D11, and a pair of lower ribs 6133 that are integrally formed with the front edge of the front portion peripheral wall portion 612 and the lower face of the base portion 6131 and extend in the forward direction D11. The front edges of the upper rib 6132 and the lower rib 6133 are located further rearward than the front edge of the base portion 6131. The portion of the front edge of the base portion 6131 where the upper rib 6132 and the lower rib 6133 are not provided is inserted into the through hole 2455 of the front side fixing portion 245, and thereby the front portion engaged portion 613 is engaged with the front side fixing portion 245 to be locked and fixed.

As shown in FIGS. 6A and 6B, a support wall portion 615 is provided on the upper face of the front portion bottom portion 611 of the member front portion 61. The support wall portion 615 is composed of a substantially triangular wall portion extending in the forward/backward direction D1 and projecting in the upper direction D21. The upper edge of the support wall portion 615 abuts with the lower wall 24 when the central fixed member 6 is fixed to the lower wall 24.

In the member front portion 61A, a through hole 616 extending in the left/right direction is formed rearward of the portion where the central through hole 601 is formed. The through hole 616 has a width and a length that are slightly longer than the width and the length of the detection central convex portion 247 in bottom view. When the central fixed member 6 is fixed to the lower wall 24, the detection central convex portion 247 is inserted into the through hole 616.

At the rear edge of the member rear portion 62, the rear portion engaged portion 623 projecting in the upper direction D21 is integrally formed with and integrally connected to a rear portion bottom portion 621. The rear portion engaged portion 623 includes a rectangular plate-like portion 6231 that is longer than the member rear portion 62 in the left/right direction D3. At the end portions of the upper end portion of the plate-like portion 6231, the locked plate portions 6232, which extend obliquely from the upper end edge of the plate-like portion 6231 in the backward direction D12 and the downward direction D22, are integrally formed with the plate-like portion 6231 to be integrally connected. When the central fixed member 6 is fitted into the front side fixing portion 245 and the rear side fixing portion 246, the locked plate portions 6232 slide on the inclined faces 2465, pass over the front end edges of the inclined faces 2465, enter the lower sides of the lower walls 2463, and the rear portion engaged portion 623 is engaged with the rear side fixing portion 246 to be locked and fixed.

The lower wall 24 constituting the bottom portion is provided with groove portions 7 serving as abutting portions. The groove portions 7 respectively abut with a plurality of kinematic pins. The kinematic pins are provided at the load port (not shown) for conveying the substrates W stored in the substrate storing space 27 to the processing apparatus, as a plurality of alignment portions, and align the container main body 2 with the load port. By abutting with the kinematic pins, the substrate storing container 1 is aligned in the forward/backward direction D1, the left/light direction D3, and the upper/lower direction D2.

Three groove portions 7 are provided at three positions of the lower wall 24 at intervals forming a center angle of about 120° in bottom view along the outer face of the lower wall 24 around the front portion of the central through hole 601. The groove portions 7 are formed such that the grooves of all of the groove portions 7 are directed toward the central through hole 601.

As shown in FIG. 1, etc., the lid body 3 has a substantially rectangular shape that substantially matches the shape of the opening circumferential portion 28 of the container main body 2. The lid body 3 is removably attached to the opening circumferential portion 28 of the container main body 2. By the lid body 3 being attached to the opening circumferential portion 28, the lid body 3 can close the container main body opening portion 21. An annular seal member 4 is attached to an inner face of the lid body 3 (a face on the back side of the lid body 3 shown in FIG. 1) that faces a face (a seal face 281) of a step portion formed at a position immediately rearward (backward direction D12) of the opening circumferential portion 28 when the lid body 3 closes the container main body opening portion 21. The seal member 4 may be made of various types of thermoplastic elastomers such as polyester type and polyolefin type that are elastically deformable, fluorine containing rubber, silicon rubber, or the like. The sealing member 4 is arranged so as to go around the circumferential edge portion of the lid body 3.

When the lid body 3 is attached to the opening circumferential portion 28, the sealing member 4 is sandwiched between the sealing face 281 and the inner face of the lid body 3 to be elastically deformed, and thus the lid body 3 closes the container main body opening portion 21 in an airtight state. By the lid body 3 being removed from the opening circumferential portion 28, it is possible to load or unload the substrates W relative to the substrate storing space 27 in the container main body 2.

A latching mechanism is provided at the lid body 3. The latching mechanism is provided in the vicinity of both left and right end portions of the lid body 3. As shown in FIG. 1, the latching mechanism includes two upper side latch portions 32A and 32B that can project from the upper side of the lid body 3 in the upper direction D21 and two lower side latch portions (not shown) that can project from the lower side of the lid body 3 in the lower direction D22. The two upper side latch portions 32A and 32B are arranged in the vicinity of both left and right ends of the upper side of the lid body 3, and the two lower side latch portions are arranged in the vicinity of both left and right ends of the lower side of the lid body 3.

An operation portion 33 is provided at an outer face of the lid body 3. By operating the operation portion 33 from the front side of the lid body 3, it is possible to cause the upper side latch portions 32A and 32B and the lower side latch portions (not shown) to project from the upper side and the lower side of the lid body 3, and it is also possible to cause the upper side latch portions 32A and 32B and the lower side latch portions (not shown) not to project from the upper side and the lower side of the lid body 3. By the upper side latch portions 32A and 32B projecting from the upper side of the lid body 3 in the upper direction D21 to engage with the latch engagement concave portions 40A and 40B of the container main body 2, and the lower side latch portions (not shown) projecting from the lower side of the lid body 3 in the lower direction D22 to engage with the latch engagement concave portions 41A and 41B of the container main body 2, the lid body 3 is fixed to the opening circumferential portion 28 of the container main body 2.

On the inner side of the lid body 3 (opposite side to the outer face of the lid body 3 appearing in FIG. 1), a concave portion (not shown) which is concave outward of the substrate storing space 27 is formed. A front retainer (not shown) is fixed to the concave portion (not shown) and a portion outside the concave portion in the lid body 3.

The front retainer (not shown) includes front retainer substrate receiving portions (not shown). The front retainer substrate receiving portions (not shown) are disposed two by two so as to form a pair and at a predetermined interval in the left/right direction D3. The front retainer substrate receiving portions disposed two by two so as to form a pair as described above are provided in a state in which 25 pairs are arranged in parallel in the upper/lower direction D2. The front retainer substrate receiving portions sandwich and support the end edges of edge portions of the substrates W by the substrates W being stored in the substrate storing space 27 and the lid body 3 being closed.

According to the substrate storing container 1 of the present embodiment having the above-described configuration, the following effects can be obtained.

As described above, in the substrate storing container 1, the central fixed member 6 is provided to the wall portion 20 of the container main body 2 so as to be removably attached to the wall portion 20 of the container main body 2. The central fixed member 6 is configured to be locked and fixed to the boss constituting the container fixing portion provided at the load port for conveying the substrates W stored in the substrate storing space 27 to the processing apparatus.

This configuration makes it possible to avoid causing an undercut when the injection mold for molding the container body 2 is released. This makes it possible to avoid providing a complicated structure called a slide structure in the mold, and to avoid complicating the operation of the mold. This eliminates the need to reduce the operation speed to prevent breakage of the mold, and makes it possible to avoid lengthening the molding cycle and lower production efficiency. Further, this makes it possible to avoid a complicated structure of the mold, and to form a cooling circuit for the mold for circulating cooling water in the mold to absorb the heat of the molten resin as an optimal circuit at an optimal position. This makes it possible to avoid extending the cooling time.

The central fixed member 6 is fixed to the wall portion 20 of the container body 2 by a fitting structure. This makes it possible to easily realize a configuration in which the central fixed member 6 can be removably attached to the wall portion 20 of the container main body 2.

The central fixed member 6 includes the member front portion 61 having an oval shape constituting a portion of the central fixed member 6 on one end portion side of the container main body 2, and the member rear portion 62 having a rectangular shape constituting a portion of the central fixed member 6 on the other end portion side of the container main body 2. The member front portion 61 is engaged with and fixed to the container main body 2 at one position, the member rear portion 62 is engaged with and fixed to the container main body 2 at two positions, and the central fixed member 6 is fitted into the wall portion 20 of the container main body 2.

This configuration enables the central fixed member 6 to be easily fitted into the lower wall 24 of the container body 2. In addition, the above-described shape enables good fluidity of the resin and good moldability. Further, the above-described shape makes it possible to make the packaging bag less likely to break when the substrate storing container 1 is packaged and transported.

The central fixed member 6 is made of a polycarbonate resin. The central fixed member 6 is made of a cycloolefin polymer resin. This configuration enables the central fixed member 6 to have a low water absorption rate, a low moisture absorption rate, and a low outgassing amount.

The present invention is not limited to the above-described embodiment, and modifications thereto within the technical scope claimed in the claims are possible. For example, the shapes of the container main body and the lid body and the number and dimensions of the substrates W that can be stored in the container main body are not limited to the shapes of the container main body 2 and the lid body 3 and the number and dimensions of the substrates W that can be stored in the container main body 2 according to the present embodiment. For example, the configuration such as the shape of the central fixed member or the like is not limited to the configuration such as the shape of the central fixed member 6 according to the present embodiment.

EXPLANATION OF REFERENCE NUMERALS 1 substrate storing container
2 container main body
3 lid body
4 central fixed member
20 wall portion
21 container main body opening portion
22 back wall
23 upper wall
24 lower wall (bottom portion)
25 first side wall
26 second side wall
27 substrate storing space
61 member front portion
62 member rear portion
W substrate

The invention claimed is:

1. A substrate storing container, comprising:
a container main body including a tubular wall portion having an opening circumferential portion provided at one end portion and the other end portion being closed, the opening circumferential portion having a container main body opening portion formed therein, and a substrate storing space formed by an inner face of the wall portion, the substrate storing space being capable of storing a substrate and communicating with the container main body opening portion;
a lid body removably attached to the opening circumferential portion and closing the container main body opening portion by being in a positional relationship in which the lid body is surrounded by the opening circumferential portion; and
a sealing member attached to the lid body and abutting with the lid body and the opening circumferential portion, the sealing member being configured to close the container main body opening portion in cooperation with the lid body by being interposed between the opening circumferential portion and the lid body so as to tightly abut with the opening circumferential portion and the lid body,
wherein the wall portion includes a back wall, an upper wall, a lower wall, and a pair of side walls; the back wall closes the other end portion of the wall portion; and one end portion of the upper wall, one end portion of the lower wall, and one end portions of the side walls form the container main body opening portion,
wherein a front end portion and a rear end portion of a central fixed member are provided to the wall portion of the container main body so as to be removably fixed to a central portion of the lower wall by being engaged with or disengaged with the central portion of the lower wall of the wall portion of the container main body, the central fixed member being configured to be locked and fixed to an alignment portion provided at a load port for conveying the substrate stored in the substrate storing space to a processing apparatus, and
wherein a front side fixing portion and a rear side fixing portion are disposed at the central portion of the lower wall, the front side fixing portion and the rear side fixing portion are configured to removably fix the central fixed member.

2. The substrate storing container according to claim 1, wherein the central fixed member is fixed to the wall portion of the container main body by a fitting structure.

3. The substrate storing container according to claim 2, wherein the central fixed member comprises:
a member front portion having an oval shape constituting a portion of the central fixed member on one end portion side of the container main body; and
a member rear portion having a rectangular shape constituting a portion of the central fixed member on the other end portion side of the container main body.

4. The substrate storing container according to claim 3, wherein the member front portion is engaged with and fixed to the container main body at one position, the member rear portion is engaged with and fixed to the container main body at two positions, and the central fixed member is fitted into the wall portion of the container main body.

5. The substrate storing container according to claim 1, wherein the central fixed member is made of a polycarbonate resin.

6. The substrate storing container according to claim 1, wherein the central fixed member is made of a cycloolefin polymer resin.

* * * * *